United States Patent [19]
DeRogatis

[11] 3,990,709
[45] Nov. 9, 1976

[54] GOLFER'S ELBOW STIFFENER

[76] Inventor: Vincent J. DeRogatis, 1913 NE. 4th St., Deerfield Beach, Fla. 33441

[22] Filed: Aug. 1, 1975

[21] Appl. No.: 600,977

[52] U.S. Cl. ............................... 273/189 A; 128/77
[51] Int. Cl.² ........................................ A63B 69/36
[58] Field of Search .......... 273/189 R, 189 A, 32 R, 273/54 B; 128/77

[56] References Cited
UNITED STATES PATENTS

| | | | |
|---|---|---|---|
| 1,469,315 | 10/1923 | Hansard | 273/189 A |
| 2,468,580 | 4/1949 | Weis et al. | 273/189 A |
| 3,238,939 | 3/1966 | Stubbs | 273/54 B |
| 3,588,105 | 6/1971 | Donohoe | 273/32 R |

FOREIGN PATENTS OR APPLICATIONS 477,944   10/1951   Canada............................ 273/189 A

*Primary Examiner*—George J. Marlo
*Attorney, Agent, or Firm*—Oltman and Flynn

[57] ABSTRACT

A golfer's elbow stiffener comprising fabric material having a series of pockets containing stiffening strips and a cover detachably fastened over the pockets and stiffening strips. The fabric material and the stiffening strips are adapted to encircle a golfer's elbow for bracing the elbow on all sides to keep it straight when swinging. The stiffening strips are easily removed from the pockets upon detaching the cover so that the fabric material may be cleaned.

8 Claims, 5 Drawing Figures

U.S. Patent  Nov. 9, 1976  3,990,709
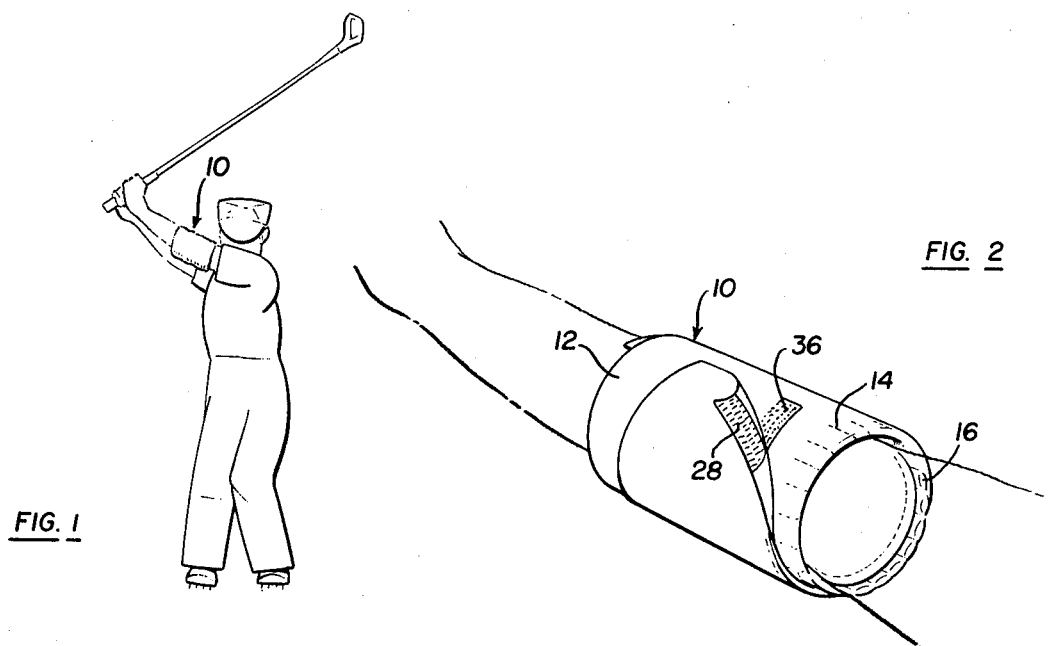
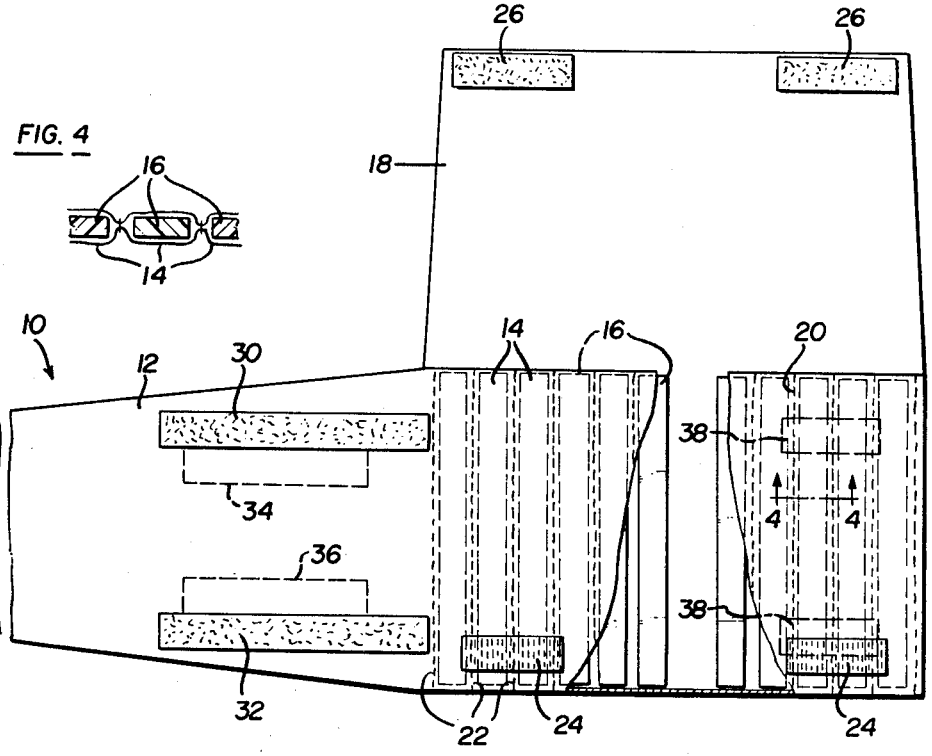
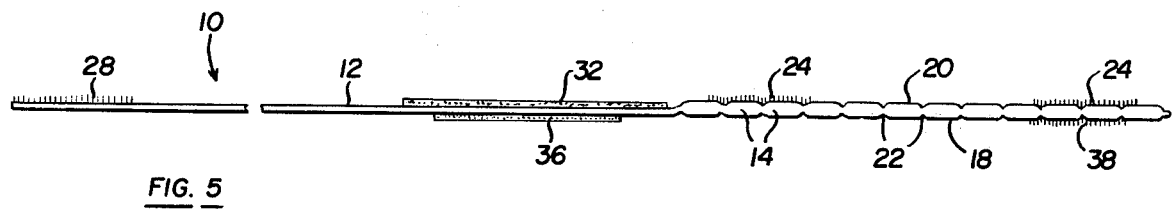

GOLFER'S ELBOW STIFFENER

BACKGROUND OF THE INVENTION

Elbow stiffening devices for use by golfers have been proposed previously. Known devices have included stiffening strips which brace only a selected portion or portions of the golfer's elbow. Also, known devices have been difficult to clean.

SUMMARY OF THE INVENTION

The golfer's elbow stiffener of the present invention completely encircles the golfer's elbow with a series of relatively rigid stiffening strips so that the elbow is firmly braced when the golfer swings. The stiffening strips are provided in a series of adjoining pockets in an elongated piece of fabric and are covered with a detachable cover. The fabric material will give slightly when worn on the elbow to allow only a slight bending of the elbow. Thus, the elbow stiffener keeps the golfer's elbow almost, but not quite, perfectly straight. This is believed to be the optimum straightening effect. The stiffening strips can be removed easily for cleaning purposes by opening the cover of the fabric.

Accordingly, it is an object of the present invention to provide an improved golfer's elbow stiffener which holds the golfer's elbow in an optimum straightened condition.

Another object of the invention is to provide rigid stiffening strips in a golfer's elbow stiffener which completely encircle the golfer's elbow.

Another object of the invention is to make the elbow stiffener of fabric material which is easily washed.

Another object is to make the stiffener slightly stretchable.

Still another object of the invention is to enable the stiffening strips to be completely enclosed when the elbow stiffener is worn and easily removed from the fabric material when the fabric material is to be washed.

Further objects and advantages of this invention will be apparent from the following detailed description of a presently-preferred embodiment thereof, which is shown in the accompanying drawings.

BRIEF DESCRIPTION OF THE DRAWINGS

FIG. 1 is a view of a golfer wearing an elbow stiffener in accordance with a preferred embodiment of the present invention;

FIG. 2 is a perspective view of the golfer's elbow stiffener as it appears when worn on the elbow of the golfer's arm;

FIG. 3 is an elevational view of the golfer's elbow stiffener showing a cover of the stiffener in an open condition;

FIG. 4 is a fragmentary sectional view taken along line 4—4 of FIG. 3 and looking in the direction of the arrows; and FIG. 5 is a bottom plan view of the elbow stiffener.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION

It is well known among golfers that for a good swing, the golfer, if right-handed, should keep his left elbow straight. However, a very slight amount of bending of the left elbow is permissable to keep the elbow from being frozen in too rigid a position. The present invention is directed to an elbow stiffener which, when worn by a golfer on his left elbow, will help him to keep his left elbow almost, but not quite, completely straight. A left-handed golfer will wear the stiffener on his right elbow.

The elbow stiffener 10 is shown as it appears on a golfer's arm in FIGS. 1 and 2. It includes an elongated piece of fabric 12 that is wrapped around the golfer's left elbow. The fabric material has pockets 14 which contain rigid stiffening strips 16. The stiffening strips 16 extend longitudinally of the golfer's arm and are located close to each other so as to provide a continuous series of stiffening strips completely encircling the golfer's elbow in the manner shown in FIG. 2. Thus, the golfer's elbow is braced on all sides when the stiffener is worn. The golfer can bend his elbow only very slightly due to the stretchable nature of the fabric material 12. Preferably, the entire length of each stiffening strip 16 is disposed within its pocket 14.

Referring to FIGS. 3–5, the fabric 12 is long enough to be wrapped twice around the golfer's elbow. It is sufficiently wide to extend about 2 inches on either side of the elbow when the elbow is centered within it. The fabric is preferably a stretch knit; for example, a single knit material. The fabric 12 includes a transverse extension 18 which forms a cover for the pockets 14 and stiffening strips 16. In this embodiment there are eleven of the stiffening strips 16 occupying all of the pockets 14 except the one which directly overlies the point of the wearer's elbow. Each strip is about ½ inch wide, 6 inches long and ¼ inch thick. The strips 16 are preferably made of a relatively rigid plastic material. It will be understood, howeveer, that the dimensions and materials may vary.

The pockets 14 are preferably formed by providing a second transverse extension 20 on the fabric 12, folding the extension 20 toward the extension 18 so that it laps over the longitudinal axis of the fabric piece 12, and stitching the extension 20 to the main body of the fabric piece 12 along the pocket edges 22.

In the preferred embodiment two spaced apart strips 24 of Velcro material are secured to the extension 20 near the bottom edge of the pockets 14 as viewed in FIG. 3. Two similarly positioned strips 26 of Velcro material are secured along the top edge of the cover 18. In the illustrated embodiment, the strips 24 have hooked fastening projections and the strips 26 are a fleecy pile fabric. Each strip 26 is pressed on the corresponding strip 24 to close the cover, thus keeping the stiffening strips 16 securely in place. The cover 18 can be easily opened so that the strips 16 can be removed from pockets 14 and the fabric can be washed.

Two Velcro strips 28 are secured to the left end of fabric piece 12 on the front side. Two Velcro strips 30 and 32 are secured to the front side of the fabric piece 12 at the left end of the pockets 14 in FIG. 3. On the back side of the fabric piece and at the left end of the pockets 14 in FIG. 3 there are two further Velcro strips 34 and 36 in substantial alignment with the strips 28 on the front side. Also on the back side of fabric piece 12, two more Velcro strips 38 are located near the right end of the pockets 14 in FIG. 3 in substantial alignment with the strips 30, 32 on the front side. Strips 34, 36 and 38 preferably have hooked projections and strips 28, 30 and 32 are preferably fleecy pile material. All of the Velcro strips 28, 30, 32, 34, 36 and 38 preferably are stitched to the fabric piece 12, and each of these Velcro strips is elongated in a direction longitudinally of the fabric piece 12, circumferentially of the wearer's arm, and substantially perpendicular to the length of the stiffening strips 16.

When placing the stiffener 10 on a golfer's arm, the pockets 14 are first wrapped around the golfer's arm and the strips 30 and 32 on the front of the fabric piece are secured to the corresponding strips 38 on the back. Because of the elongation of these strips along the length of the fabric piece 12, different sized arms are accommodated. Then the left end of the fabric piece 12 is wrapped around the golfer's elbow and the strips 28 on the front side are fastened to the corresponding strips 34 and 36 on the back. Thus, there is a double thickness of material on the golfer's elbow. The elongation of strips 28, 34 and 36 allows for variation in size.

I claim:

1. In a golfer's elbow stiffener in which stiffening strips are adapted to be held on a golfer's elbow, the improvement comprising:
   an elongated piece of stretchable fabric sufficiently long to be wrapped twice around an arm of the golfer at the elbow;
   means forming a series of adjoining open-ended pockets toward one end of said fabric piece leaving the other end portion of said fabric piece without pockets;
   said pockets each extending transversely of said fabric piece, and said series of pockets extending a distance longitudinally of said fabric piece to encircle the golfer's arm at the elbow when said stiffener is worn;
   a rigid stiffening strip in each of said pockets except a middle-pocket which directly overlies the point of the golfer's elbow;
   a single, unitary, foldable cover means for releasably closing all of said pockets; and
   means for fastening said piece around the arm at the elbow.

2. The stiffener as claimed in claim 1 in which said fabric comprises stretchable knit material.

3. The stiffener as claimed in claim 1 in which:
   said foldable cover means comprises a single transverse extension of said fabric piece foldable over open ends of said pockets; and
   fasteners secured to said extension and said pockets to retain said extension closed and allow opening thereof, with said stiffening strips being removable from said pockets when said extension is open.

4. The stiffener as claimed in claim 3 in which said fasteners comprise fabric fasteners of hook and pile material.

5. The stiffener as claimed in claim 4 in which:
   said fastening means comprises a first set of fabric fasteners including complementary hook and pile strips located respectively adjacent opposite ends of said series of pockets and on opposite sides of said fabric piece; and
   a second set of fabric fasteners including complementary hook and pile strips located respectively on opposite sides of said fabric piece adjacent one end of said series of pockets and said other end portion of said fabric piece;
   said fabric piece being sufficiently long to provide a double thickness of fabric around the arm at the golfer's elbow with double fastenings therefor provided by said first and second sets of fasteners.

6. The stiffener as claimed in claim 5 in which:
   the strips of said first and second sets are elongated longitudinally of said fabric piece to accommodate different sized wearers' arms.

7. The stiffener as claimed in claim 6 in which:
   said pockets are formed by stitching in a second transverse extension of said fabric piece folded over the main body thereof.

8. The stiffener as claimed in claim 7 in which said fabric comprises stretchable knit material.

* * * * *